United States Patent [19]

Akatsuka

[11] 4,116,797
[45] Sep. 26, 1978

[54] OXYGEN SENSOR

[75] Inventor: Takao Akatsuka, Toyota, Japan

[73] Assignee: Toyota Jidosha Kogyo Kabushiki Kaisha, Toyota, Japan

[21] Appl. No.: 799,694

[22] Filed: May 23, 1977

[30] Foreign Application Priority Data

Dec. 3, 1976 [JP] Japan .................. 51/145326

[51] Int. Cl.$^2$ .......................................... G01N 27/46
[52] U.S. Cl. ......................... 204/195 S; 55/486; 55/487; 55/527; 55/528
[58] Field of Search ............... 204/15, 195 S; 55/486, 55/487, 527, 528

[56] References Cited

U.S. PATENT DOCUMENTS

| | | | |
|---|---|---|---|
| 2,146,071 | 2/1939 | Horvath | 55/487 |
| 2,594,793 | 4/1952 | Muerle | 55/487 |
| 2,822,059 | 2/1958 | Lunn et al. | 55/487 |
| 3,455,792 | 7/1969 | Ohta | 55/528 |
| 3,720,594 | 3/1973 | Wilson | 204/195 S |
| 3,960,693 | 6/1976 | Weyl et al. | 204/195 S |
| 4,019,974 | 4/1977 | Weyl et al. | 204/195 S |

FOREIGN PATENT DOCUMENTS 2,454,339  5/1975  Fed. Rep. of Germany ....... 204/195 S

*Primary Examiner*—T. Tung
*Attorney, Agent, or Firm*—Brisebois & Kruger

[57] ABSTRACT

An oxygen sensor to be used with internal combustion engines, in automobiles, etc.. The sensor includes a solid electrolyte tube with a closed tip, an outer and an inner electrode respectively formed on the outside and the inside of the electrolyte tube, a housing to hold the tube, electrically conductive means to take out the electrical output of the inner metal electrode, a cover supported by the housing; an air passage in an end opening of the cover; and a multi-layer heat-resistant filter with a low rate of thermal expansion in the air passage.

11 Claims, 2 Drawing Figures

OXYGEN SENSOR

BACKGROUND OF THE INVENTION

Air pollution with exhaust gas from the internal combustion engines of automobiles and the like is not a new problem and it is now assuming the proportions of a social issue. Air pollution with exhaust gas is mainly attributable to unburnt hydrocarbons (hereafter called unburnt HC), carbon monoxide (hereafter called CO) and nitrogen oxides (hereinafter called NOx) contained in the exhaust gas. To render these contents of the gas harmless, various measures have been tried. To mention a few examples, there are purification systems utilizing an oxidizing catalyst, a reducing catalyst or a combination of these two. Also known is a system for simultaneous treatment of the three elements (three-way system) which can treat the unburnt HC, CO and NOx at the same time through reaction of them with a special catalyst under specific conditions. This three-way system is an excellent system and exhibits high purifying ability in the theoretical air/fuel ratio range. To maintain the theoretical air/fuel ratio range, the oxygen concentration of the exhaust gas in the exhaust system must be monitored so that the fuel jet volume in the engine can in turn be controlled. An oxygen sensor is used to monitor the oxygen concentration of the exhaust gas in the exhaust system.

The oxygen sensor takes the form of an oxygen concentration cell composed of a solid electrolyte which is made of a special ceramic material having oxygen-ion conductivity. The electromotive force or voltage generated through a difference in the oxygen partial pressure between the gas to be analyzed and a reference gas, is measured, and the oxygen concentration of the gas to be analyzed is determined from the measured voltage.

As the reference oxygen for the oxygen sensor, oxygen gas itself, or a metal oxide-metal can be employed. For the purpose of detecting the oxygen concentration in exhaust gas, it is convenient to use atmospheric air as the reference gas, i.e., the gas with the higher concentration of oxygen and the exhaust gas as the gas with the lower concentration of oxygen. In the oxygen sensor using atmospheric air as the reference gas, the air has to be admitted to the reference gas electrode and accordingly an air passage to introduce the air is provided in the oxygen sensor.

However, for the measurement of oxygen concentration in the exhaust gas, the oxygen sensor is installed in the engine room or compartment, etc., of an automobile where it is exposed to water, mud, etc., which can enter through the air passage and which could damage a heated sensor ceramic, or adversely affect the action of the electrodes.

SUMMARY OF THE INVENTION

A principle object of the present invention is to provide an oxygen sensor which is free from entry or invasion of water, mud, etc.

Another object of the present invention is to provide an oxygen sensor in which water, mud, etc., cannot damage a heated sensor ceramic or adversely affect the action between electrodes of the sensor.

Still another object of the present invention is to provide an oxygen sensor which is protected from direct exposure to mud, which could cause a clogging of its filter.

Other objects of the present invention will become more apparent from the attached drawings and the following detailed description.

DETAILED DESCRIPTION OF THE INVENTION

The oxygen sensor, according to the present invention, has a multi-layer filter assembly at the air passage through which atmospheric air is introduced as the reference gas. The layers of the filter are preferably made of a porous heat-resistant material with a low rate of thermal expansion, which preferably does not deform nor significantly expand in the temperature range of $-40°\sim+200°$ C. TEFLON (poly-tetrafluoroethylene), which is heat-resistant, has a low rate of thermal expansion, and is highly water-repellent, is notably preferable. Depending on the service temperature, porous forms of substances such as polyfluoroethylene, polyethylene, polypropylene, polyurethane, and nylon can be used, and molded inorgnaic fibers such as glass wool, and rock wool are also usable.

While the filter may be made in any form, it can be a porous plastic molding of these substances alone or in combination.

This oxygen sensor utilizing the atmospheric air as the reference oxygen gas can take the form of a tip-closed tube of solid electrolyte with the inside surface exposed to atmospheric air as the reference oxygen gas and the outside surface exposed to the exhaust gas; an inner electrode formed on the inside of the tube; an outer electrode formed on the outside of the tube; a housing to hold the tube of solid electrolyte and which housing includes a means to attach the sensor to the car body or exhaust system; electrically conductive means to take out the voltage output of the inner electrode; a cover supported by the housing; and an air passage provided in the end opening of the cover. In such a sensor, the solid electrolyte consists of a special ceramic material which is liable to break and to protect it a tubular protective cover is provided following the housing.

Now one preferred embodiment will be described, referring to FIG. 1, which is a sectional view of an oxygen sensor according to the present invention.

When the oxygen sensor is equipped with a waterproof cover 9 as mentioned above, there is usually no direct exposure to mud and clogging of the filter can be avoided.

Figure 2:
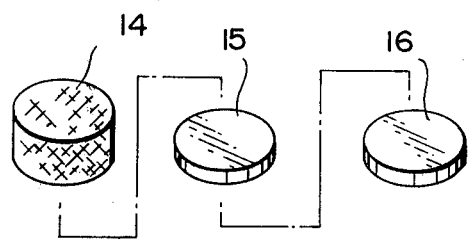
FIG. 2 is an enlarged, exploded pictorial view of the filter assembly of the oxygen sensor of FIG. 1.

The filter assembly 8 which supplies the atmosphere to the inner electrode consists of, as indicated in FIG. 2 from top to bottom (outside to the inside of cover 4), a glasswool filter 14, a Teflon filter 15 with large pore size or diameter, and a Teflon filter 16 with small pore size or diameter superposed together, and which capture progressively coarse to fine dust and other foreign matter, thereby resisting clogging of the filter assembly. The number of filter layers and their pore diameters depend on the service conditions of the oxygen sensor, presence or absence of a waterproof cover, and the material quality of the filters. In one preferred form, the filter assembly 8 can be composed of a glasswool filter 14, a Teflon filter 15 about 1mm thick with 100µ (micron) to 200µ (micron) fibrous screen pores, and a Teflon filter 16 about 6mm thick with numerous small pores of 1µ size or diameter.

The solid electrolyte which forms the tube 3 can be any oxygen-ion conductive material, but a $ZrO_2$— base ceramic material, for example, $ZrO_2$—$Y_2O_3$, can be used. $HfO_2$, $UO_2$, $ThO_2$ or $CeO_2$ can be used instead of $ZrO_2$; $CaO$, $MgO$, $Sc_2O_3$ or $Nd_2O_3$, can be used instead of $Y_2O_3$.

As the material to form the metal electrodes 17, 18 on the inside and outside of the solid electrolyte tube, platinum, in a form which does not adversely affect the oxygen-ion conductivity of the electrolyte tube 3 is appropriate.

The oxygen sensor includes a metal housing 2 with a reduced diameter lower end which can be threaded to facilitate installing the sensor in an exhaust system, like a spark plug. Housing 2 is counter-sunk from its upper end to provide an upwardly facing conical shoulder. A solid electrolyte tube 3 is disposed withing the housing and has a conical shoulder facing toward the conical shoulder of the housing. Electrolyte tube 3 is held securely in the housing 2 by a spring 5 which extends around an electrically conductive metal piece or pipe 13 and engages a shoulder of an enlargement of the piece 13 to hold the electrolyte tube in engagement with the conical shoulder of the housing. The piece 13 has a through opening 12 providing an air path.

Secured to the upper portion of the housing is an elongated cover sleeve 4. A plug shaped electrical insulator 6, within cover sleeve 4, is secured to the cover sleeve for example, by crimping the cover sleeve into a groove of the insulator as shown at FIG. 1. This insulator is of heat resistant material and is located at approximately the vertical mid-point of the height of the cover sleeve.

The upper open end of cover sleeve 4 is closed by an inserted packing or plug 7 made of an electrically insulating material, like rubber or plastic, and which is resistant to deterioration at temperatures as high as 200° C. The packing 7 has a through hole providing an air passage containing a filter assembly 8. The top end of cover sleeve 4 is covered with a waterproof cover or cap 9 having an air hole 10.

On the outside of electrolyte tube 3 is an outer electrode 18, and on the inside of the tube is an inner electrode 17. The electrodes 17 and 18 on the inside and outside of the solid electrolyte tube are preferably platinum, and electrode 18 can be covered with a porous coating of an inorganic substance.

Figure 1:
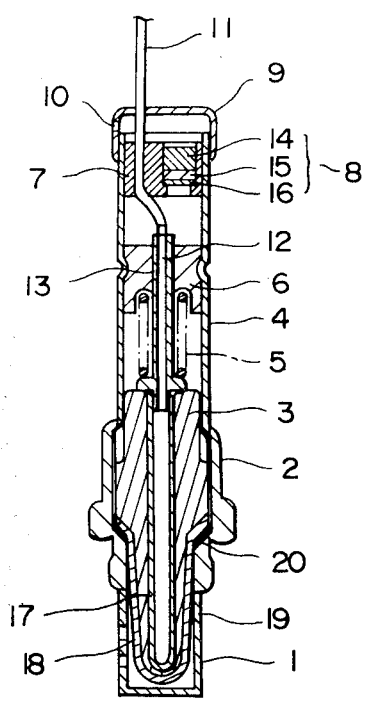
FIG. 1 is an elevational view in section of an oxygen sensor according to the present invention.

As shown at FIG. 1, outer electrode 18 extends onto the conical shoulder of electrolyte tube 3. At this shoulder, between the outer electrode 18 and the housing 2, is a high temperature resistant electrically conductive packing such as a graphite sheet 20, which electrically connects electrode 18 to housing 2 and seals the electrolyte tube to the housing. With the oxygen sensor installed in, for example, an exhaust manifold, it is apparent that outer electrode 18 is grounded to the automobile via the electrical path including graphite sheet 20 and the metal housing 2.

The electrode 18 on the outside of the lower closed end of the tube 3, is exposed to the exhaust gas. A protective ceramic cover 1, secured to the lower end of housing 2, protects the lower end of the electrolyte tube. Ceramic cover 1 has numerous apertures 19 formed therein to permit exhaust gas to pass through and into contact with the lower outer portion of the tube.

As shown at FIG. 1, inner electrode 17 extends to the upper end of electrolyte tube 3 and is electrically connected to conductive piece 13 which extends into the electrolyte tube and engages electrode 17. A lead wire 11, secured to the upper end of conductive piece 13, but which does not block air path 12, extends through packing 7 and cap 9.

As is evident with reference to FIG. 1, the upper end of spring 5 seats on the bottom surface of insulator 6 and presses conductive piece 13 against electrolyte tube 3 which in turn presses electrolyte tube 3 against graphite sheet 20 and the shoulder of housing 2 to firmly hold the assembly in position in the housing, while permitting axial and slight radial expansion of the electrolyte tube with respect to the housing. As is evident from FIG. 1, there is no need for the connection between cover sleeve 4 and insulator 6 to be air tight, and the exterior of conductive piece 13 need not be an air tight fit in insulator 6. The graphite sheet 20 which functions as a packing, prevents any air in the region above the sheet 20 from flowing down to contact outer electrode 18, and similarly prevents any exhaust gas from flowing upwardly into the region above the graphite packing.

As a result of the configuration and construction of the electrolyte tube 3 and the housing 2, where the tube 3 engages the housing only at the conical shoulder where graphite packing 20 is located, there in no other engagement between the tube and the housing, and clearance is provided between the tube 3 and the cover sleeve 4. This assures the absence of binding between the cover sleeve and tube 3, and assures that the outer electrode touches the housing 2 only at packing 20. The conical shoulders maintain the electrolyte tube 3 centered in the housing 2.

As described above, the oxygen sensor according to the present invention, which can introduce the air without permitting the invasion of water, mud, etc., has a number of merits such as being able to serve for a long period without damage to the ceramic electrolyte tube and without any adverse effect on the action between electrodes, or the ability to make measurements with stability.

What is claimed is:

1. An automotive exhaust system oxygen sensor utilizing atmospheric oxygen as a reference gas, comprising, a solid electrolyte tube with a closed tip; an outer electrode and an inner electrode formed respectively, on the outside and the inside of said tube; a housing supporting said tube; electrically conductive means to take out the output of said inner electrode; a cover supported by said housing; means defining an air passage at an end of said cover; and a multi-layer filter provided in said air passage, said filter comprising a heat-resistant material with a low rate of thermal expansion, and said filter excluding water, dust and other foreign matter from contact with said inner electrode.

2. An oxygen sensor according to claim 1, wherein a packing of an electrically insulating material closes an end opening of the cover, said packing having a through opening defining said air passage and containing said multi-layer filter.

3. An oxygen sensor according to claim 1, wherein the end of the cover outwardly of said air passage is capped with a waterproof closure having an air hole.

4. An oxygen sensor according to claim 3, wherein a tubular ceramic-protecting cover extends around the closed tip of the electrolyte tube.

5. An oxygen sensor according to claim 1, wherein the solid electrolyte tube is made of a ceramic material composed of a compound selected from the group of $ZrO_2$, $HFO_2$, $UO_2$, $THO_2$ and $CeO_2$; and a compound selected from the group of $Y_2O_3$, CaO, MgO, $Sc_2O_3$ and $Nd_2O_3$.

6. An oxygen sensor according to claim 1, wherein said material of the multi-layer filter does not change or remarkably expand in the temperature range of $-40°$ to $+200°$ C.

7. An oxygen sensor according to claim 1 wherein said filter material comprises a heat-resistant, low rate of thermal expansion material, selected from the group of polyfluoroethylene, polyethylene, polypropylene, polyurethane, nylon, glasswool and rockwool.

8. An oxygen sensor according to claim 1, wherein said filter material comprises polytetrafluoroethylene.

9. An oxygen sensor according to claim 1, wherein said multi-layer filter comprises three layers of filter material.

10. An oxygen sensor according to claim 9, wherein said three filter layers comprise from outside to inside, an outer glasswool filter; a first polytetrafluoroethylene inner filter with large pore diameter; and a second polytetrafluoroethylene filter with small pore diameter.

11. An oxygen sensor according to claim 10, wherein said first polytetrafluoroethylene filter is about 1mm thick with $100\mu$ to $200\mu$ fibrous screen pores; and said second polytetrafluoroethylene filter is about 6mm thick with numerous small pores of $1\mu$ size.

* * * * *